(12) United States Patent
Spindler et al.

(10) Patent No.: US 12,139,796 B2
(45) Date of Patent: Nov. 12, 2024

(54) NANOSTRUCTURE AND METHOD FOR PRODUCING SAME

(71) Applicants: KARLSRUHER INSTITUT FÜR TECHNOLOGIE, Karlsruhe (DE); Bruno Spindler, Oppenau (DE)

(72) Inventors: Bruno Spindler, Oppenau (DE); Patrick Doll, Karlsruhe (DE); Ralf Ahrens, Karlsruhe (DE); Andreas Guber, Karlsruhe (DE)

(*) Notice: Subject to any disclaimer, the term of this patent is extended or adjusted under 35 U.S.C. 154(b) by 166 days.

(21) Appl. No.: 17/624,363

(22) PCT Filed: Jul. 2, 2020

(86) PCT No.: PCT/DE2020/000148
§ 371 (c)(1),
(2) Date: Jan. 3, 2022

(87) PCT Pub. No.: WO2021/000982
PCT Pub. Date: Jan. 7, 2021

(65) Prior Publication Data
US 2022/0282363 A1 Sep. 8, 2022

(30) Foreign Application Priority Data
Jul. 3, 2019 (DE) .................. 10 2019 004 577.7

(51) Int. Cl.
*C23C 8/16* (2006.01)
*C01G 23/04* (2006.01)
(Continued)

(52) U.S. Cl.
CPC ............. *C23C 8/16* (2013.01); *C01G 23/04* (2013.01); *B82Y 30/00* (2013.01); *B82Y 40/00* (2013.01);
(Continued)

(58) Field of Classification Search
None
See application file for complete search history.

(56) References Cited

U.S. PATENT DOCUMENTS

| 5,952,114 A | 9/1999 | Gunji et al. |
| 2010/0159118 A1 | 6/2010 | Hayakawa et al. |
| (Continued) | | |

FOREIGN PATENT DOCUMENTS

| CN | 105689709 A | * 6/2016 |
| DE | 19612434 C2 | 10/1996 |
| (Continued) | | |

OTHER PUBLICATIONS

Bhadra, Chris M., et al. "Antibacterial titanium nano-patterned arrays inspired by dragonfly wings." Scientific reports 5.1 (2015): 1-12.

*Primary Examiner* — Daniel J. Schleis
(74) *Attorney, Agent, or Firm* — Smartpat PLC

(57) ABSTRACT

A nanostructure is made of a plurality of nanocrystals on at least one surface or surface region of a titanium body. A method for generating such nanostructure is by means of hydrothermal oxidation. Thereby, the nanocrystals have a basic tetragonal-pyramidal shape, at least in some regions. The area density of the nanocrystals is between 40 and 400 per $\mu m^2$, wherein the area density decreases with increasing crystal height. The average spacing of 50 to 160 nm of adjacent nanocrystals is obtained at a nanocrystal height of 23 to 100 nm. This provides a titanium-based, bactericidal and hydrophilic nanostructure for implant surfaces and, at the same time, a corresponding manufacturing method with which the size and distribution of the nanocrystals forming a nanostructure that facilitates healing can be determined.

9 Claims, 4 Drawing Sheets

(51) Int. Cl.
*B82Y 30/00* (2011.01)
*B82Y 40/00* (2011.01)

(52) U.S. Cl.
CPC ...... *C01P 2002/60* (2013.01); *C01P 2004/30* (2013.01)

(56) References Cited

U.S. PATENT DOCUMENTS

| | | |
|---|---|---|
| 2011/0218643 A1 | 9/2011 | Yerokhin |
| 2014/0329052 A1 | 11/2014 | Ibacache et al. |
| 2014/0342316 A1 | 11/2014 | Berner et al. |

FOREIGN PATENT DOCUMENTS

| | | |
|---|---|---|
| EP | 2156851 A1 | 2/2010 |
| EP | 2212453 B1 | 7/2012 |
| WO | 2013056844 A1 | 4/2013 |
| WO | 2013086336 A1 | 6/2013 |

\* cited by examiner

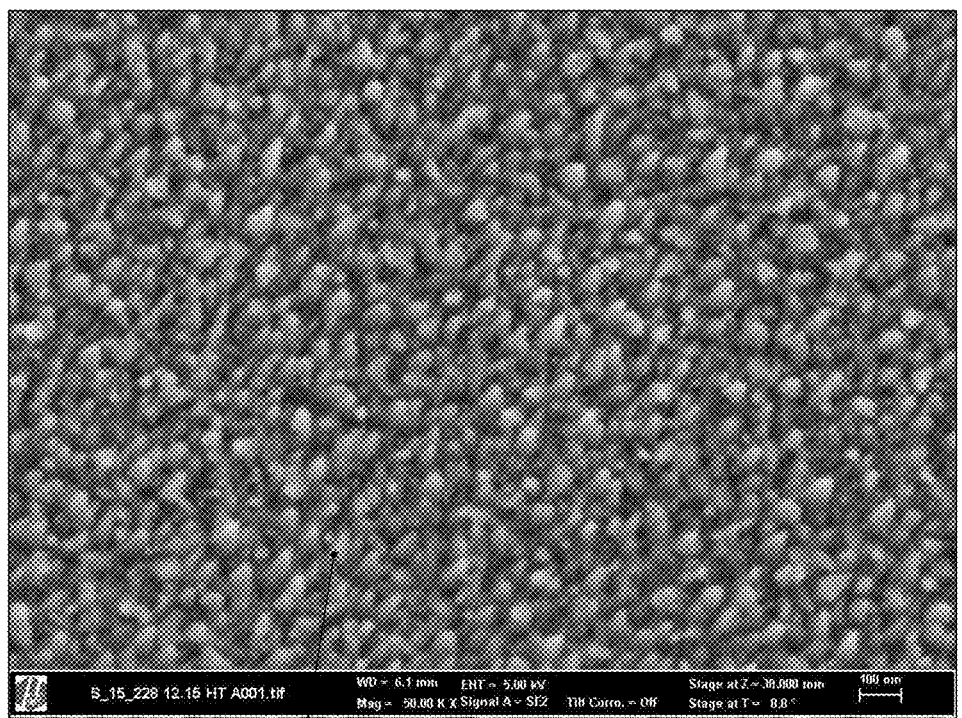
39  Fig. 4
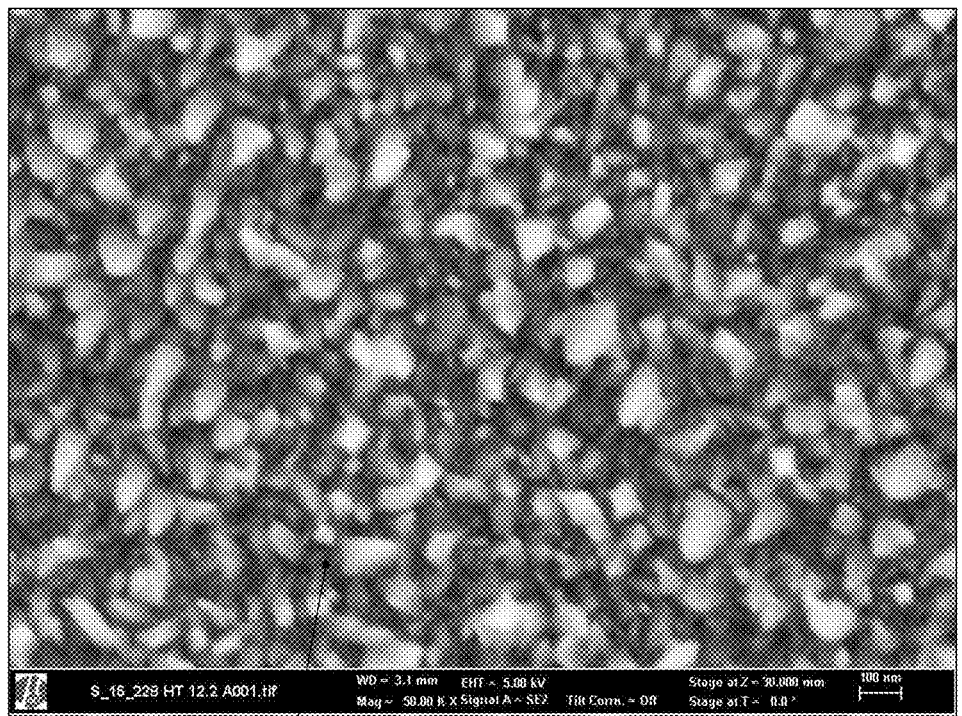
39  Fig. 5

NANOSTRUCTURE AND METHOD FOR PRODUCING SAME

TECHNICAL FIELD

The disclosure relates to a nanostructure made of a plurality of nanocrystals on at least one surface or one surface region of a titanium body, and to a method for generating such nanostructure by hydrothermal oxidation.

BACKGROUND

An important prerequisite for successful and long-term implant integration in the human body is stable anchoring of the implant in the respective bone. The implant must be osseointegrated, that is, be in direct functional bone contact. Titanium and titanium alloys, among others, are used as implant materials. These have proven suitable due to their biocompatibility, their chemical inertness and their excellent corrosion resistance. During implantation and the unit phase commencing immediately afterwards, protection against the bacterial colonization of germs is particularly important. To prevent the development of undesirable biofilms, there is, among other things, the possibility of a medicinal coating or the use of antibacterial surfaces.

In the Nov. 18, 2015, scientific reports article entitled "Antibacterial titanium nano-patterned arrays inspired by dragonfly wings" by authors Chris M. Bhadra, Vi Khanh Truong, Vy T. H. Pham, Mohammad Al Kobaisi, Gediminas Seniutinas, James Y. Wang, Saulius Juodkazis, Russell J. Crawford and Elena P. Ivanova the fabrication of an antibacterial nanostructure is described. In this process, a mechanically roughened titanium specimen surface is hydrothermally oxidized in a potassium hydroxide solution for one hour at a pressure of 1.7 to $2.03*10^5$ PA and at a temperature of 121° C. Oxidation is followed by hot air heat treatment at 400° C. for three hours.

This method produces a fragile and brittle nanostructure. If the surface is stressed, for example when implanting a prosthetic denture, there is a possibility that countless titanium oxide nanoparticles will break out of the nanostructure. Their toxic effect often causes inflammation of the implant bed and associated bone loss in the corresponding jaw region.

SUMMARY

The present disclosure develops a titanium-based, bactericidal and hydrophilic nanostructure for implant surfaces and, at the same time, provides a corresponding manufacturing method with which the size and distribution of the nanocrystals forming a nanostructure that facilitates healing can be determined.

The nanostructure is made of a plurality of nanocrystals on at least one surface or surface region of a titanium body. The nanocrystals have a basic tetragonal-pyramidal shape, at least in some regions. The area density of the nanocrystals is between 40 and 400 per $\mu m^2$, wherein the area density decreases with increasing crystal height. The average spacing of 50 to 160 nm of adjacent nanocrystals is obtained at a nanocrystal height of 23 to 100 nm.

A method for generating a nanostructure on at least one surface or surface region of a titanium body is by hydrothermal oxidation. For this purpose, the initial surface for nanostructure generation is exposed to a 160 to 374.12° C. hot vapor pressure atmosphere, wherein the vapor-forming medium is demineralized water. Thereby, the nanocrystal area density and the nanocrystal size along with the color of the oxide layer of the nanostructure are each a function of the vapor pressure exposure time, wherein—at the given vapor pressure temperature range—for a usable area density and size of the nanocrystals, the exposure time is 1 to 100 h.

The surface topography generated by this method has compact and stable nanocrystals that do not tend to break or chip during implantation if handled properly. On the one hand, due to its roughness, the topography favors the attachment of eukaryotic cells such as, in particular, fibroblasts and/or endothelial cells. In this manner, for example, gum growth can be accelerated after denture implantation. On the other hand, the surface topography that is generated hinders increased colonization of gram-negative bacteria. These include the rod-shaped bacterium *Pseudomonas aeruginosa*, a typical hospital pathogen that is now resistant to several antibiotics.

Such bacteria interact with the nanostructure. According to the currently valid model, adsorption of the cell membrane between the nanostructures occurs due to surface effects. The adsorption is based, among other things, on the hydrophilic property of the presented nanostructure, which gives it an above-average surface wettability.

During adsorption, the sharp-edged nanocrystals of the nanostructure injure the cell membrane of the respective bacterium. The rupture of the cell membrane inevitably leads to the death of the bacterium, since the cell plasma flows out of the ruptured cell membrane.

Experiments with the described nanostructures have shown that gram-negative *Escherichia coli* bacteria colonizing a titanium sample can be rendered harmless after a two-hour incubation—through the contact killing present here.

The nanostructures shown in the exemplary embodiment example can be created on almost any 3D free-form surface. The supporting substrate of the base material can have a macrostructure and/or microstructure. All nanostructures described are not coatings of a base material.

BRIEF DESCRIPTION OF THE DRAWINGS

FIG. 4: Scanning electron microscope image of a nanostructure after crystal growth at 220° C. for 24 hours.

FIG. 5: Scanning electron microscope image of a nanostructure after crystal growth at 220° C. for 96 hours.

DETAILED DESCRIPTION

Figure 1:
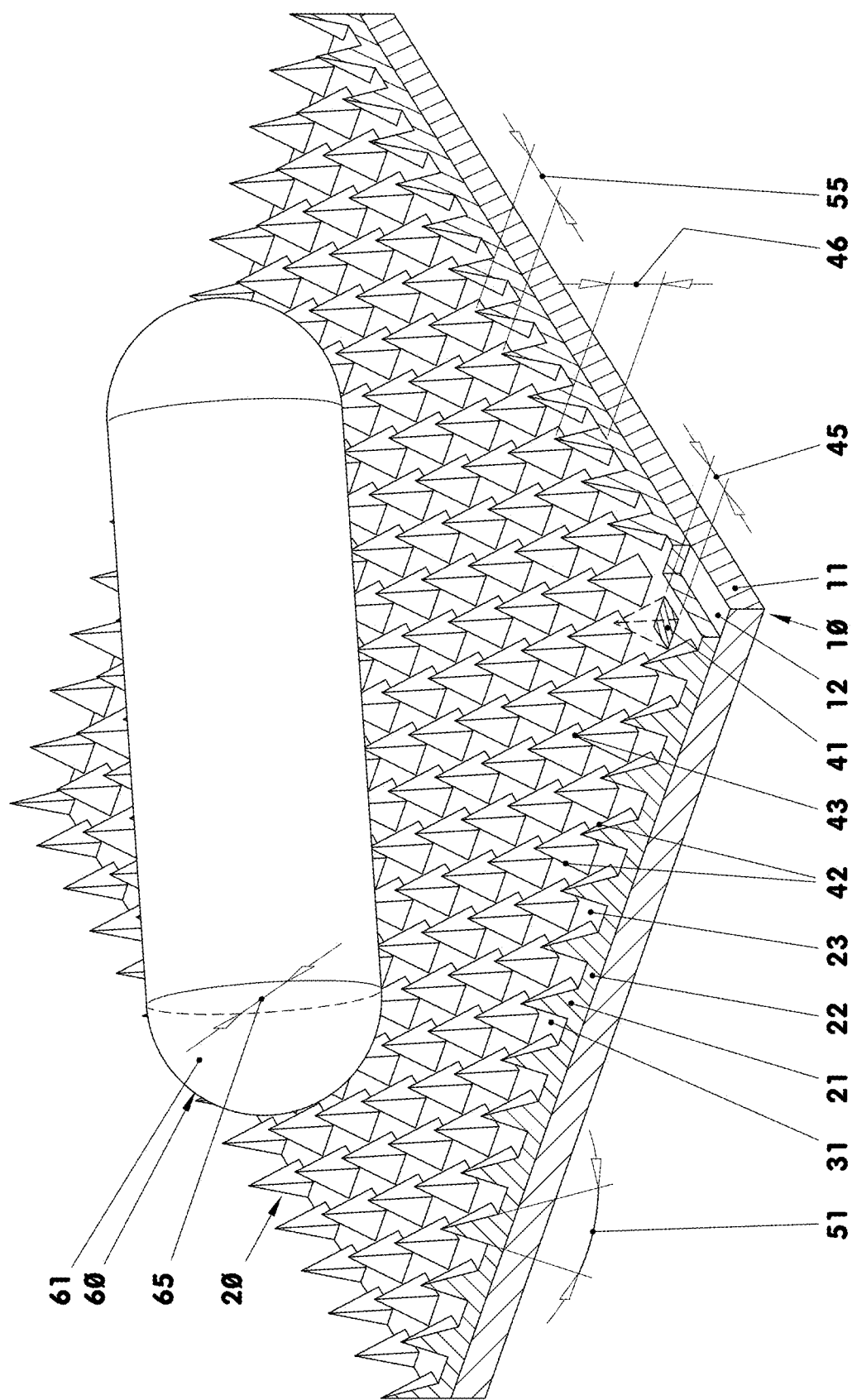
FIG. 1: Perspective view of a bacterium on an ideal nanostructure made of tetragonal-pyramidal nano-crystals.
Figure 2:
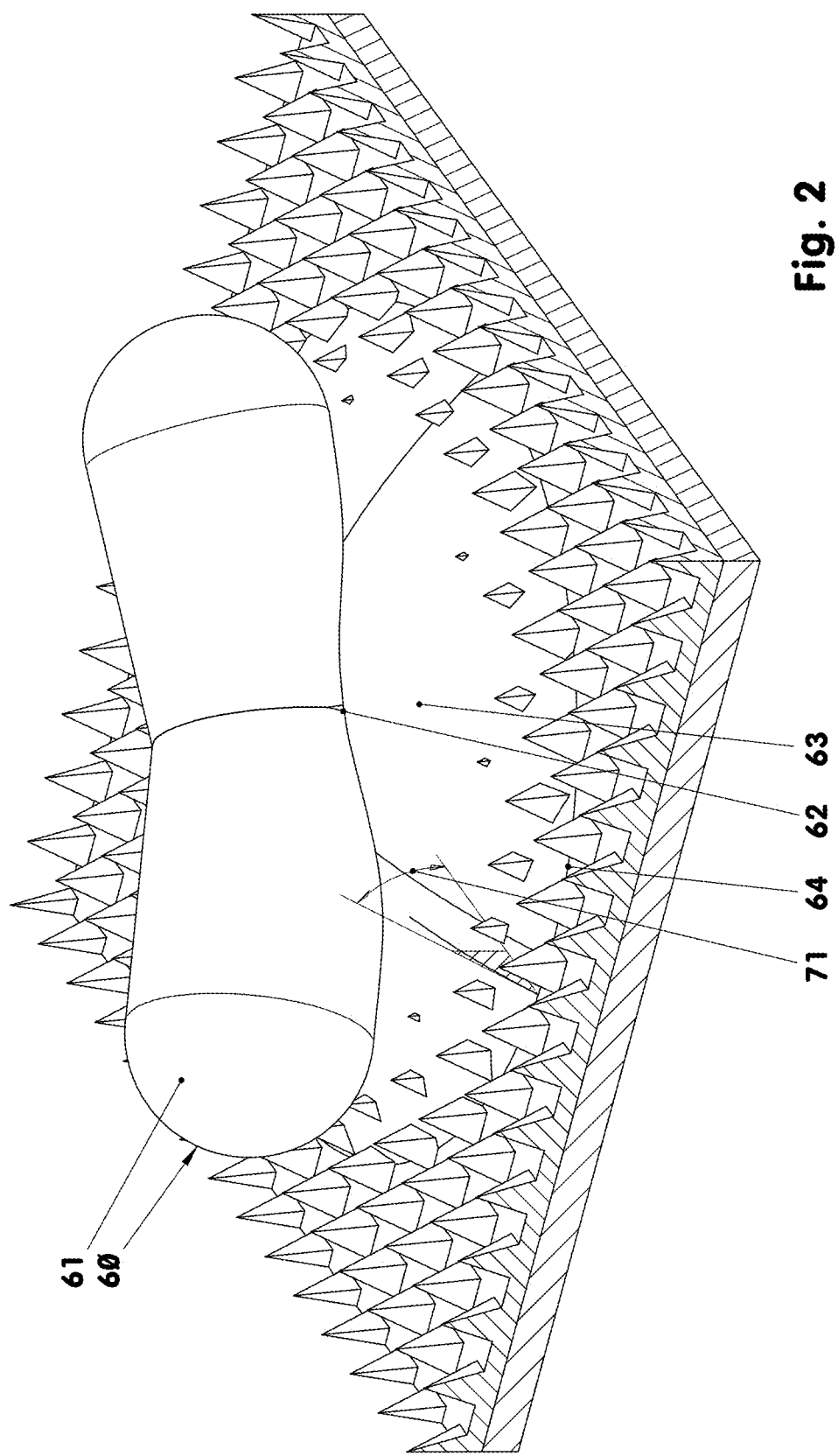
FIG. 2: As FIG. 1, but with a bacterium whose cell membrane has ruptured immediately beforehand.

FIGS. 1 and 2 show—in the form of a technical drawing with regard to the geometry, but not the size ratios—an enlarged view of an outer region of an implant body (10), the surface area of which corresponds to 1 $\mu m^2$. A substantially cylindrical bacterium (60) attempts to colonize this bio-inspired surface. The surface is covered with a bactericidal and hydrophilic nanostructure (20) generated on a base body (11) of pure titanium (grade 4) or a titanium alloy Ti6Al4V ELI (grade 23).

The nanostructure (20) is generated with the aid of hydrothermal oxidation. The latter represents a method with which oxidation of the implant body (10) is carried out in the presence of an aqueous solution under high pressure and temperature. The oxidation takes place in a steam-tight sealed pressure vessel. The pressure vessel is heated to, for example, 220° C. together with the inserted implant body (10), a certain amount of aqueous solution such as ultrapure water or demineralized water and an addition of oxygen required for oxidation. If necessary, the oxygen content in the pressure vessel can be additionally increased or decreased.

The vapor pressure developing in the pressure vessel is accompanied by a shift in the thermodynamic equilibrium of the respective crystallization reaction. Crystal growth occurs on the surface of the implant body (10) accessible to the steam. The result is a nanotopography of stable crystals, which preferably grow almost vertically out of the base material, see FIG. 3.

According to FIGS. 1 and 2, the base body (11) has, for example, a flat base surface (12) from which the hydrothermal oxidation causes the nanocrystals (40) to grow out. Thereby, a growth layer (21) has built up over this base surface (12), from which the nanocrystals (40) protrude. Between the large nanocrystals (40), which are depicted as pyramids, a flat bottom enveloping surface (23) is shown—idealized here. The region below the bottom enveloping surface (23) is the bottom layer (22).

FIGS. 1 and 2 show pure geometric surfaces according to DIN 4760.

The size of the real nanocrystals (40) is a function of the retention period of the titanium body (10) in the pressure vessel. With increasing retention period, the nanostructure usually grows with an increase in the size of the nanocrystals (40) and a simultaneous decrease in their distribution density. Below is a table showing the geometric dimensions after three retention periods. The retention periods are 6, 24 and 96 h.

Figure 3:
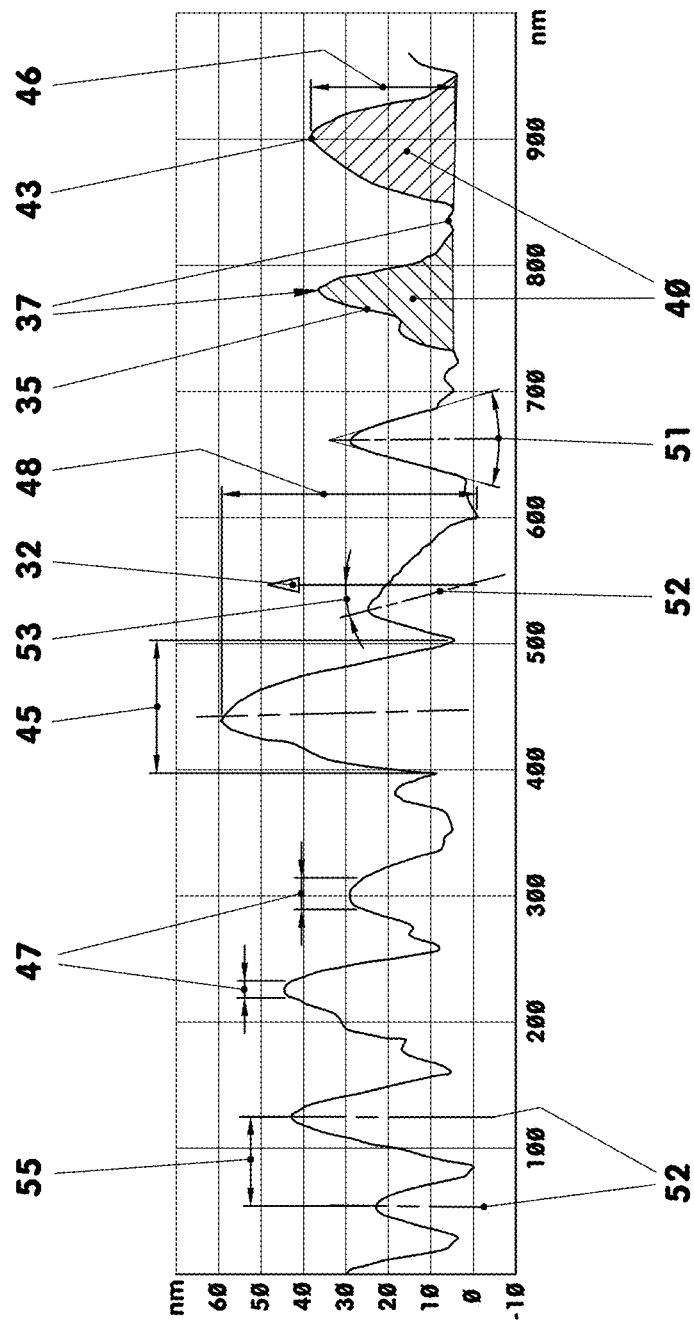
FIG. 3: Profile illustration of a real nanostructure whose surface is measured with an atomic force microscope.

| Time [h] | Density [1/μm²] | Spacing [nm] | Height [nm] | Base width [nm] | Angle [°] | Diameter [nm] |
|---|---|---|---|---|---|---|
| 6 h. | 308 | 57.0 | 23.3 ± 6.2 | 74.1 ± 9.5 | 27.6 ± 11.6 | 19.1 ± 2.2 |
| 24 h | 220 | 67.4 | 41.9 ± 13.6 | 84.4 ± 9.7 | 31.0 ± 10.8 | 23.4 ± 4.0 |
| 96 h | 100 | 100 | 74.2 ± 13.6 | 100.1 ± 20.6 | 35.4 ± 11.0 | 35.7 ± 6.5 |
| Reference signs in FIGS. 1-3: | | (55) | (46) | (45) | (51) | (47) |

The distribution or area density is denoted by "density" in the table. The "spacing" denotes the average spacing between two adjacent nanocrystals (40), see also FIG. 3. The "height" indicates the total height of a nanocrystal (40) above the bottom enveloping surface (23). The "base width" is the width of the base surface (41) of a nanocrystal (40). The "angle" reflects the pyramid angle of the nanocrystals (40). The "diameter" is a measure of the width of the tip of a real nanocrystal (40). It is measured for the nanocrystal (40) at a height above the bottom enveloping surface (23) corresponding to 85 to 95% of the total nanocrystal height. The "diameter" refers to a circumference parallel to the base surface (12) that at least two edges of a real nanocrystal (40) contact. Thereby, the percentage lower limit applies especially to nanocrystals (40) with large pyramidal angle and small total height.

The geometry ratios of the illustrations of FIGS. 1 and 2 apply to a titanium body (10) made of the titanium alloy Ti6Al4V, the crystal growth of which lasted 96 h at a pressure vessel temperature of 220° C. This also applies to the profile illustration according to FIG. 3.

FIGS. 1 and 2 show the wall thickness of the growth layer (21). It is the shortest spacing between the base surface (12) and the bottom enveloping surface (23). It measures 0.33±30% of such fraction of the average height (46) of the nanocrystals (40) overhanging the bottom enveloping surface (23). The base surfaces (41) of the nanocrystals (40) are located in the bottom enveloping surface (23).

According to FIG. 1, a gram-negative bacterium (60) lies on the nanostructure (20)—on the diagonal of the section shown. As an example, the bacterium Pseudomonas aeruginosa, whose external shape generally consists of a straight cylindrical or a weakly curved torus segment-shaped cell wall with hemispherical ends, is shown in simplified form. The diameter (65) of the bacterium (60) is 0.5 to 1.0 μm, while its length measures 1.5 to 5.0 μm. The bacterium (60) has a cell wall with a wall thickness of approximately 2 nm. Thus, the cell wall thickness is less than 1.2% of the average height (46) of the nanocrystals (40) shown by way of example. In FIGS. 1 and 2, the bacterial flagella are not shown.

The bacterium (60) attaching itself to the titanium body (10) contacts the nanostructure (20), according to FIG. 1, only in the region of the nanocrystal tips (43).

FIG. 2 shows the bacterium (60) immediately after the first contact with the nanostructure (20) damaging the cell membrane (61). The cell membrane (61) has a first tear (62) in the central region of the bacterium (60), through which the cell plasma (63) leaks out—for example, under a buckling of the bacterium (60) in its central region—and spreads between the nanocrystals (40) on the bottom enveloping surface (23).

After only a short time, the cell membrane (61) has largely deflated, such that it rests as an empty shell on the nanostructure (20) without protruding appreciably beyond the tips (43) of the nanocrystals (40).

A contact angle (71) is shown in FIG. 2 by way of example only. The contact angle (71) or marginal or wetting angle is a measure of the wettability of a solid surface with a liquid. The interaction between the implant surface and the wetting liquid is large for nanostructures (20) with the geometry values of the table reproduced above, such that the liquid hitting the nanostructure (20), including bacteria (60) and their cytoplasm (63), is sucked between the nanocrystals (40). In the exemplary embodiment, the contact angle (71) is less than 20 angular degrees.

FIG. 3 shows a real profile section (35) perpendicular to the flat base surface (12). According to DIN 4760, it is a surface that has been measured with an atomic force microscope. By mechanically scanning the real surface (39), see FIGS. 4 and 5, with a nanoscopically small needle, almost all sharp-edged transitions are reproduced in rounded form. In the diagram, the height values of the nanostructure are plotted on the abscissa, while the corresponding transverse expansions are plotted on the ordinate—along the length of a micrometer. In addition to nanocrystal sizes such as spacing (55), tip diameter (47), base width (45), pyramid angle (51), and height (46), a nanocrystal center line (52) with the corresponding angle of inclination (53) is also shown. The angle of inclination (53) drawn here is, for example, 15 angular degrees. All other geometry values can be taken from the above table—with the exception of the spacing (55)—of the third content line as mean values.

FIGS. 4 and 5 show two top views of real surfaces of dimension 2.2*1.5 µm, see scale on the right, below. In FIG. 4, the retention period in the pressure vessel is 24 hours. The corresponding geometry values are shown in the second content line of the above table.

FIG. 5 shows a top view of a nanostructure that was in the pressure vessel at a temperature of 220° C. for 96 h. Their geometry values can be found in the third content row of the above table.

The top views demonstrate the presence of the generally sharp-edged nanocrystals, which have grown predominantly perpendicular to the base surface (12). A uniform distribution of the nanocrystals protruding from the bottom envelope surface can also be seen, such that the individual surface topographies can be specifically adapted to the respective intended use. The nanostructures are reproducible with high repeatability if the respective predefinable process parameters are adhered to.

LIST OF REFERENCE SIGNS

10 Implant body, titanium body
11 Base body
12 Base surface, initial upper surface, initial surface
20 Nanostructure
21 Growth layer
22 Base layer
23 Bottom enveloping surface
31 Geometry surface, geometric surface
32 Normal direction
35 Profile section, section line
37 Actual surface, detectable by measurement technology
39 Real surface, true surface
40 Nanocrystals
41 Base surface
42 Nanocrystal edge
43 Nanocrystal tip, tip, tip region
45 Base width, width
46 Height, total height, total nanocrystal height
47 Tip diameter, diameter
48 Roughness profile height $R_z$ according to DIN EN ISO 4287
51 Pyramid angle, angle
52 Nanocrystal center line, center line
53 Angle of inclination
55 Spacing between two larger nanocrystals
60 Bacterium
61 Cell membrane, cell wall
62 Rupture, tear
63 Cell plasma
64 Edge from (63) to (23)
65 Diameter
71 Contact angle

The invention claimed is:

1. A nanostructure (20) made of a plurality of nanocrystals on at least one surface (39) or surface region of a titanium body (10),
    wherein the nanocrystals (40) have a tetragonal-pyramidal basic shape, at least in some regions,
    wherein an area density of the nanocrystals (40) per µm$^2$ is between 40 and 400, wherein the area density decreases with increasing crystal size, and
    wherein an average spacing between adjacent nanocrystals (40) at a height of 23 to 100 nm is 50 to 160 nm.

2. The nanostructure according to claim 1,
    wherein at least 60% of the nanocrystals (40) have a square, quadrilateral, rectangular, rhombic, parallelogram-shaped, trapezoidal, or kite-shaped base surface (41).

3. The nanostructure according to claim 2,
    wherein the nanocrystals (40) have a pyramid angle (51) of 16 to 46 angular degrees.

4. The nanostructure according to claim 2,
    wherein the nanocrystals (40) have a base width (45) of 50 to 150 nm.

5. The nanostructure according to claim 2,
    wherein a tip region of the nanocrystals (40) has, at a height corresponding to 85 to 95% of the total nanocrystal height (46), a circumference that is parallel to the base surface (12) and has a diameter of 10 to 50 nm, against which at least two nanocrystal edges (42) abut.

6. The nanostructure according to claim 2,
    wherein an angle of inclination (53) of the nanocrystals (40) lying between a normal direction (32) of the base surface (12) and a center line (52) of the individual nanocrystal (40) is less than 30 angular degrees.

7. The nanostructure according to claim 1,
    wherein the area density of the nanocrystals refers to the nanocrystals (40) whose total height (46) is greater than 0.3 times the maximum roughness profile height (48).

8. A method for generating a nanostructure (20) made of tetragonal-pyramidal nanocrystals on at least one surface (39) or surface region of a titanium body (10) by means of hydrothermal oxidation to form an oxide layer, comprising:
    exposing an initial surface (12) for nanostructure generation to a 160 to 374.12° C. hot vapor pressure atmosphere for a vapor pressure exposure time from 1 to 100 h,
    wherein a vapor-forming medium is demineralized water, and
    wherein a nanocrystal area density and a nanocrystal size along with a color of the oxide layer of the nanostructure (20) are each a function of the vapor pressure exposure time.

9. The method according to claim 8,
    wherein in that the demineralized water contains a hydrogen absorbing additive.

* * * * *